(12) United States Patent
Mårtensson

(10) Patent No.: US 7,670,416 B2
(45) Date of Patent: *Mar. 2, 2010

(54) USE OF A COMBINATION OF SUBSTANCES TO PREVENT BIOFOULING ORGANISMS

(75) Inventor: Lena Mårtensson, Kungälv (SE)

(73) Assignee: I-Tech AB

( * ) Notice: Subject to any disclaimer, the term of this patent is extended or adjusted under 35 U.S.C. 154(b) by 0 days.

This patent is subject to a terminal disclaimer.

(21) Appl. No.: 11/497,454

(22) Filed: Aug. 1, 2006

(65) Prior Publication Data

US 2007/0028825 A1 Feb. 8, 2007

Related U.S. Application Data

(60) Provisional application No. 60/705,321, filed on Aug. 4, 2005.

(51) Int. Cl.
*C09D 5/16* (2006.01)
*A01N 43/48* (2006.01)
*A01N 43/50* (2006.01)

(52) U.S. Cl. ............... 106/18.32; 106/15.05; 106/18.34; 106/18.35; 106/18.36; 424/78.09; 424/405; 514/184; 514/360; 514/372; 514/396; 523/122; 523/179

(58) Field of Classification Search ............... 106/15.05, 106/18.32, 18.34, 18.35, 18.36; 424/638, 424/641, 78.09, 405; 514/94, 184, 360, 372, 514/396; 523/122, 179
See application file for complete search history.

(56) References Cited

U.S. PATENT DOCUMENTS

| 5,397,385 A * | 3/1995 | Watts ....................... 106/18.32 |
| 5,629,045 A * | 5/1997 | Veech ......................... 427/297 |
| 6,762,227 B1 * | 7/2004 | Elwing et al. ............... 524/106 |

OTHER PUBLICATIONS

Dahlstrom Mia et al., "Impact of Polymer Surface Affinity of Novel Antifouling Agents", Biotechnology and Bioengineering 86(1), pp. 1-8 (Apr. 5, 2004).*
Derwent-Acc-No. 2005-109811, abstract of Swedish Patent Specification No. 200300863A (Sep. 29, 2004).*

* cited by examiner

*Primary Examiner*—Anthony J Green
(74) *Attorney, Agent, or Firm*—Lynn E. Barber

(57) ABSTRACT

A combination of selected substances in paint to prevent the settlement and growth of different bio-fouling organisms with a reduced negative effect on the ecosystems compared to present methods. Useful substances include medetomidine with various copper and zinc formulations, tolylfluanide, diclofluanide, DIURON™ and IRGAROL™, or more general biocides such as SEANINE™ (4,5-dichloro-2-n-octyl-3 (2H)-isothiazolone) or ECONEA™ (2-(p-chlorophenyl)-3-cyano-4-bromo-5-trifluoromethyl pyrrole).

14 Claims, No Drawings

USE OF A COMBINATION OF SUBSTANCES TO PREVENT BIOFOULING ORGANISMS

CROSS-REFERENCE TO RELATED APPLICATIONS

This application claims priority from U.S. provisional patent application Ser. No. 60/705,321 filed Aug. 4, 2005, the disclosure of which is incorporated herein by reference.

BACKGROUND OF THE INVENTION

1. Field of the Invention

This invention relates to the use of a combination of selected substances in paint to simultaneously prevent the settlement and growth of different bio-fouling organisms, such as barnacles and algae.

2. Description of the Related Art

Biological growth (or bio-fouling) on marine installations and ships constitutes a significant problem for the shipping industry and for owners of marine installations and boats and ships at large. An untreated ship hull will rapidly accumulate fouling of marine plants and animals, which considerably increases hull-to-water friction and consequently, fuel consumption. Also other marine industries and installations, e.g., aqua culture equipment and oil/gas off-shore installations and plants have significant problems with marine bio-fouling.

One way of preventing marine bio-fouling is to apply paint with toxic contents, e.g. tributyltinnoxide (TBT) or copper. The use of marine paints with such contents has, however, proven to cause significant harm to the marine ecosystem including plants, animal species and humans. (1, 2). As used herein, numbers in parentheses refer to references in the list of references herein according to standard practice. Many countries and international organizations have therefore introduced restrictions and prohibitions over their use, and further restrictions are expected. Sale and application of TBT antifouling is to cease, under the International Maritime Organization (IMO) Antifouling System Convention agreed in October 2001. The treaty calls for the ban on application from the first of January 2003, and total prohibition on hulls by the first of January 2008.

It is therefore of interest to find new solutions to prevent marine bio-fouling, to be able to reduce levels of metal and metal-oxides in paints and eventually replace them completely (3-5).

Mechanical cleaning of marine surfaces has been introduced as an alternative to toxics and biocides. Notably, water jet cleaning and mechanical cleaning using brushes are in use. Most of these methods are work-intensive, however, and are therefore expensive.

The tributyltin-ban (TBT) is a reality since the international paint companies have excluded TBT-containing paints from their product portfolio. Instead, the basic biocides are copper, copper oxide or other copper based formulations. When the copper compounds are used in reduced concentrations for ecological reasons, however, these paints need booster biocides against barnacles and algae to achieve a performance acceptable for ship owners and other types of marine industries. Also, paints with specific new compounds active mostly against barnacles, such as medetomidine ("Catemine 1") as described below, will need a complementary booster compound against algae.

Along the Swedish west coast as well as along the coasts of the North Atlantic Ocean, barnacles and different kinds of algae are particularly apparent problems. The fully grown barnacle is a stationary crustacean, characterized by a centi-meter-sized cone shape and enclosing layers of calcinous plates. The mechanical strength of the animal's attachment to solid surfaces is very high, and it is therefore difficult to mechanically remove barnacles from solid surfaces. The animal undergoes different development stages as free-swimming larvae, where the last larva stage is referred to as the cyprid stage. The cyprid screens solid surfaces suitable for settling with the help of a nervous protuberance. A "settling-glue" referred to as balanus cement is secreted from specialized glands localized near the protuberance and the animal thereby settles to the solid surface. After settlement the animal undergoes a metamorphosis into an adult and stationary animal. When using an old copper leaking paint with high concentrations of copper, barnacles are one of the first organisms to foul.

Algae are also relatively insensitive to copper and the amount of leaking copper needed to inhibit fouling of algae is high. Therefore, copper-containing marine antifouling paints are "boosted" by some manufacturers with more specific algicides. The algicides inhibit the zoospores from attaching or inhibit photosynthesis. Both methods give the result of reduced algae fouling.

Previously various compounds have been described and used that interfere with nerve signalling or other specific action against the fauna of marine bio-fouling organisms, such as barnacles or tube worms. For example, U.S. Pat. No. 6,762,227 describes the use of medetomidine (Catemine 1) and other substances. Also, Swedish patent application No. 0300863-8 describes the use of spiroimidazoline (Catemine 3) for the same purpose. However, the use of such products has no or very little effect on algae. For example, Catemine 1 (6) has a specific action on barnacle cyprids but no effect of algal growth due to the target protein being lacking within algae. This is true also for other pharmacological acting substances (7-11).

There are several methods to prevent algal growth, among them the use of copper and other metals in fairly high concentrations. Algicides are often invented as herbicides and are photosynthesis-inhibitors such as DIURON™ (3-(3,4-dichlorophenyl)-1,1-dimethylurea) by DuPont Agricultural Products Wilmington, Del., USA and IRGAROL™ 1051 (2-methylthio-4-tert-butylamino-6-cyclopropylamino-s-triziane) by Ciba Inc, Tarrytown, N.Y., USA. A more common strategy is to use fungicides such as zincpyrithione (Zinc, bis(1-hydroxy-2(1H)-pyridinethionato-O,S)—, (T-4)-) by Arc Chemicals Inc and copperpyrithione (Copper, bis(1-hydroxy-2(1H)-pyridinethionato-O,S)—, (T-4)-) by Arc Chemicals Inc, tolylfluanide (N-(Dichlorofluoromethylthio)-N',N'-dimethyl-N-p-tolylsulfamide) by Bayer Chemicals, Pittsburgh, Pa., USA, diclofluanide (N'-dimethyl-N-phenyl-sulphamide) by Bayer Chemicals, ZINEB™ (zinc ethylene bisdithiocarbamate) by FMC corp., ZINRAM™ (Zinc bis (dimethylthiocarbamates)) (3-5) by Taminco, or quaternary ammonium compounds. A third strategy is to use toxic compounds but with short half life such as SEANINE™ (4,5-dichloro-2-n-octyl-3(2H)-isothiazolone) by Rohm and Haas Company, Philadelphia, Pa., USA and related compounds (12).

A strategy that has received a lot of attention for several years is to find natural substances that may work as antifoulants in paint. These substances are endogenously produced by different marine invertebrates and algae to protect their own surface from fouling. Several compounds have been isolated and identified and their antifouling activity been measured (4).

There is a need however to find compounds, or a combination of compounds, to be applied in antifouling paint so that such paint is more effective against both types of organisms such as barnacles and algae without having as many negative ecological effects as paint with high levels of metal-compounds.

SUMMARY OF THE INVENTION

The invention at hand refers to a method which is an ecologically acceptable way to prevent both cyprid larvae and algae from establishing at solid surfaces. The old kind of bio-fouling paints with high concentrations of metals are active against both barnacles and algae, but have several negative environmental effects. A reduced concentration of the active metal-compound in such paints will make it non-effective particular against algae and barnacles. Newer more ecological compounds, used, or proposed to be used, in antifouling are more effective against one or the other group of fouling organisms.

The present invention solves this problem by providing new and effective combinations of antifouling agents, such as medetomidine (Catemine 1) ((+/−)-4-[1-(2,3-dimethylphenyl)ethyl]-1H-imidazole) with IRGAROL™ (2-methylthio-4-tert-butylamino-6-cyclopropylamino-s-triziane), or medetomedine with Dichlofluanid and other combinations. The substance that affects nerve signaling in cyprid barnacles may also be selected from the group consisting of medetomidine and spiroimidazoline.

Other objects and features of the inventions will be more fully apparent from the following disclosure.

DETAILED DESCRIPTION OF THE INVENTION AND PREFERRED EMBODIMENTS THEREOF

The principle of the method of the invention is to use substances which disturb or block the nerve signalling to the target cells in the cyprid larvae in combination with anti-algae compounds, for example, fungicides like zinc- and copper pyrithione, tolylfluanide and diclofluanide, herbicides such as DIURON™ and IRGAROL™, or more general biocides such as SEANTNE™ or ECONEA™ (2-(p-chlorophenyl)-3-cyano-4-bromo-5-trifluoromethyl pyrrole) by Janssen Pharmaceutical, Titusville, N.J., USA.

By using low toxic biodegradable compounds as booster biocides, it will be possible to reduce the non-biodegradable copper in a paint. One such example can be to use the environmentally friendly compounds to disturb important nerve signalling in barnacles and the like, while at the same time maintain low levels of metal-compounds in combination of a biodegradable algicide, with substantially less negative effect on the environment. One important practical and industrial application of this invention is to mix these substances into a polymer base (paint). The polymer (paint) is consequently applied to ship hulls and in the seawater environment the substances will slowly release from the polymer. Settling cyprid larvae will consequently be disturbed in such a way that settling cannot take place. By the addition of a booster algicide it is also possible to prevent algal growth. The invention includes the use of relatively low toxic pharmacological substances, e.g. medetomidines, which disturb, imitate or block nerve signal processing to the cells of some organisms, for example barnacles, in settling on solid surfaces and the combination with other substances for the prevention of settlement and growth of algae which inhibit algal adhesion or growth. The immediate application of the invention is to add the substances in a base polymer paint which is later applied on e.g. ship hulls.

Example 1

The efficacy of algicides is usually tested by a spore germination test. Algae are collected from the field and grown in the laboratory. After induced sporulation the spores are added to test vials, with the test compound dissolved in pasteurized deep sea water, where they are allowed to settle in darkness for a couple of hours (2-3 h) to give an even distribution of settled spores in the vials. The water with test compound is then removed and culture medium is added. The spores are left to germinate under fluorescent lamps (50 μm-2s-1 (PAR)), 16 h light, 8 h darkness, for 7 days in a culture medium, which is changed once a day.

Catemine 1 is to be combined with an effective anti-algae compound according to the invention, such as dichlofluanid (table 1), SEANINE™ (table 2), IRGAROL™ (table 3) and DIURON™ (table 4). All the different brands are tested in combination with Catemine 1 for efficacy against both barnacles and algae with the two compounds together or separate. The assays that are be used are the cyprid settling rate assay and the algae germination test.

By using this kind of a combination, it is possible to prevent fouling from both barnacles and macroalgae and increase the total efficacy of the antifouling paint.

TABLE 1

| Catemine 1 (nM) | Dichlofluanid (μg/ml) | Barnacle biofouling (% settlement) | Ulva biofouling (% survival) |
|---|---|---|---|
| 0 | 0 | 100 | 100 |
| 0.1 | 0 | 100 | 100 |
| 1 | 0 | 10 | 100 |
| 10 | 0 | 0 | 100 |
| 100 | 0 | 0 | 100 |
| 0 | 0 | 100 | 100 |
| 0 | 0.1 | 100 | 100 |
| 0 | 1 | 50 | 90 |
| 0 | 10 | 25 | 10 |
| 0 | 100 | 0 | 0 |
| 0 | 0 | 100 | 100 |
| 0.1 | 0.1 | 100 | 100 |
| 1 | 1 | 10 | 90 |
| 10 | 10 | 0 | 10 |
| 100 | 100 | 0 | 0 |

TABLE 2

| Catemine 1 (nM) | SeaNine (nM) | Barnacle biofouling (% settlement) | Ulva biofouling (% survival) |
|---|---|---|---|
| 0 | 0 | 100 | 100 |
| 0.1 | 0 | 100 | 100 |
| 1 | 0 | 10 | 100 |
| 10 | 0 | 0 | 100 |
| 100 | 0 | 0 | 100 |
| 0 | 0 | 100 | 100 |
| 0 | 0.1 | 100 | 100 |
| 0 | 1 | 50 | 50 |
| 0 | 10 | 10 | 10 |
| 0 | 100 | 0 | 0 |
| 0 | 0 | 100 | 100 |
| 0.1 | 0.1 | 100 | 100 |
| 1 | 1 | 10 | 50 |
| 10 | 10 | 0 | 10 |
| 100 | 100 | 0 | 0 |

TABLE 3

| Catemine 1 (nM) | Irgarol (nM) | Barnacle biofouling (% settlement) | Enteromorpha biofouling (% survival) |
|---|---|---|---|
| 0 | 0 | 100 | 100 |
| 0.1 | 0 | 100 | 100 |
| 1 | 0 | 10 | 100 |
| 10 | 0 | 0 | 100 |
| 100 | 0 | 0 | 100 |
| 0 | 0 | 100 | 100 |
| 0 | 0.1 | 100 | 100 |
| 0 | 1 | 100 | 100 |
| 0 | 10 | 100 | 50 |
| 0 | 100 | 100 | 0 |
| 0 | 0 | 100 | 100 |
| 0.1 | 0.1 | 100 | 100 |
| 1 | 1 | 10 | 100 |
| 10 | 10 | 0 | 50 |
| 100 | 100 | 0 | 0 |

TABLE 4

| Catemine 1 (nM) | Diuron (μM) | Barnacle biofouling (% settlement) | Ulva biofouling (% survival) |
|---|---|---|---|
| 0 | 0 | 100 | 100 |
| 0.1 | 0 | 100 | 100 |
| 1 | 0 | 10 | 100 |
| 10 | 0 | 0 | 100 |
| 100 | 0 | 0 | 100 |
| 0 | 0 | 100 | 100 |
| 0 | 0.1 | 100 | 100 |
| 0 | 1 | 100 | 90 |
| 0 | 10 | 100 | 50 |
| 0 | 100 | 100 | 0 |
| 0 | 0 | 100 | 100 |
| 0.1 | 0.1 | 100 | 100 |
| 1 | 1 | 10 | 90 |
| 10 | 10 | 0 | 50 |
| 100 | 100 | 0 | 0 |

While the invention has been described with reference to specific embodiments, it will be appreciated that numerous variations, modifications, and embodiments are possible, and accordingly, all such variations, modifications, and embodiments are to be regarded as being within the spirit and scope of the invention.

REFERENCES

1. Ruiz, J. M., Bachelet, G., Caumette, P. and Donard, O. F. X. Three decades of tributyltin in the coastal environment with emphasis on Arachon Bay, France. Environmental Pollution 93(2) 195-203, 1996.
2. Mizuhashi, S., Ikegaya, Y. and Matsuki, N. Pharmacological property of tributyltin in vivo and in vitro. Environmental Toxicology and Pharmacology 8, 205-212, 2000.
3. Omae, I. Organotin antifouling paints and their alternatives. Appl. Organometal. Chem. 17, 81-105, 2003.
4. Omae, I. General aspects of tin-free antifouling paints. Chem. Rev. 103, 3431-3448, 2003.
5. Yebra, D. M., Kiil, S. And Dam-Johansen, K. Antifouling technology—past, present and future steps towards efficient and environmentally friendly antifouling coatings. Progress in Organic Coatings. 50, 75-104, 2004.
6. Dahlström M, Mårtensson L G E, Jonsson P R, Arnebrant T, Elwing H. Surface-active adrenoceptor compounds prevent the settlement of cyprid larvae of Balanus improvisus. Biofouling 16, 191-203, 2000
7. Yamamoto H, Tachibana A, Saikawa W, Nagano M, Matsumura K, Fusetani N. Effects of calmodulin inhibitors on cyprid larvae of the barnacle, *Balanus amphitrite*. J. Exp. Zool. 80; 8-17, 1998.
8. Yamamoto H, Satuito C G, Yamazaki M, Natoyama K, Tachibana A, Fusetani N. Neurotransmitter blockers for antifoulants against planktonic larvae of the barnacle *Balanus amphitrite* and the mussel *Mytilus gallopronvincialis*. Biofouling 13:69-82, 1998.
9. Yamamoto, H., Shimizu, K., Tachibana, A. and Fusetani, N. Roles of dopamine and serotonin in larval attachment of the barnacle, *Balanus amphitrite*. J. Exp. Zool. 284, 746-758, 1999.
10. Faimali, M., Falugi, C., Gallus, L., Piazza, V. and Tagliaferro, C. Involvement of acetylcholine in settlement of Balanus amphitrite. Biofouling 19 Suppl. 213-20, 2003.
11. Rittschof, D., Lai, C. H., Kok, L. M. and Teo, S. L. Pharmaceuticals as antifoulants: concept and principles. Biofouling 19 Suppl. 207-12, 2003.
12. Jacobson, A. H. and Willingham, G. L. Sea-nine antifoulant: an environmentally acceptable alternative to organotin antifoulants. The Science of the Total Environment 258, 103-110, 2000.

What is claimed is:

1. A method of preventing marine biofouling of a substrate by a marine biofouling organism, comprising applying a protective coating composition to the substrate, said coating composition containing a) a substance that affects nerve signaling in cyprid barnacles comprising medetomidine, and b) an algal inhibitory substance selected from the group consisting of 2-(p-chlorophenyl)-3-cyano-4-bromo-5-trifluoromethyl pyrrole, Zinc, bis(1-hydroxy-2(1H)-pyridinethionato-O,S)—, (T-4)-), N-(dichlorofluoromethylthio)-N',N'-dimethyl-N-p-tolylsulfamide, and 4,5-dichloro-2-n-octyl-3 (2H)-isothiazolone.

2. The method of preventing marine biofouling according to claim 1, wherein the algal inhibitory substance is 4,5-dichloro-2-n-octyl-3(2H)-isothiazolone).

3. The method of preventing marine biofouling according to claim 1, wherein the protective coating composition further comprises o-xylene.

4. The method of preventing marine biofouling according to claim 1, wherein the protective coating composition further comprises a marine paint.

5. The method of preventing marine biofouling according to claim 1, wherein the algal inhibitory substance is (2-(p-chlorophenyl)-3-cyano-4-bromo-5-trifluoromethyl pyrrole.

6. The method of preventing marine biofouling according to claim 1, wherein the algal inhibitory substance is Zinc, bis(1-hydroxy-2(1H)-pyridinethionato-O,S)—, (T-4)-).

7. The method of preventing marine biofouling according to claim 1, wherein the algal inhibitory substance is N-(dichlorofluoromethylthio)-N',N'-dimethyl-N-p-tolylsulfamide.

8. A product for preventing marine biofouling of a substrate by a marine biofouling organism, comprising a protective coating composition containing a) a substance that affects nerve signaling in cyprid barnacles comprising medetomidine, and b) an algal inhibitory substance selected from the group consisting of Zinc, bis(1-hydroxy-2(1H)-pyridinethionato-O,S)—, (T-4)-), N-(dichlorofluoromethylthio)-N',N'-dimethyl-N-p-tolylsulfamide; 2-(p-chlorophenyl)-3-cyano-4-bromo-5-trifluoromethyl pyrrole and 4,5-dichloro-2-n-octyl-3(2H)-isothiazolone.

9. The product for preventing marine biofouling according to claim 8, wherein the algal inhibitory substance is 4,5-dichloro-2-n-octyl-3(2H)-isothiazolone).

10. The product for preventing marine biofouling according to claim 8, wherein the protective coating composition further comprises o-xylene.

11. The product for preventing marine biofouling according to claim 8, wherein the protective coating composition further comprises a marine paint.

12. The product for preventing marine biofouling according to claim 8, wherein the algal inhibitory substance is (2-(p-chlorophenyl)-3-cyano-4-bromo-5-trifluoromethyl pyrrole.

13. The product for preventing marine biofouling according to claim 8, wherein the algal inhibitory substance is Zinc, bis(1-hydroxy-2(1H)-pyridinethionato-O,S)—, (T-4)-).

14. The product for preventing marine biofouling according to claim 8, wherein the algal inhibitory substance is N-(dichlorofluoromethylthio)-N',N'-dimethyl-N-p-tolylsulfamide.

* * * * *